(12) United States Patent
Besio

(10) Patent No.: US 8,352,012 B2
(45) Date of Patent: Jan. 8, 2013

(54) BIOMEDICAL ELECTRODE FOR DETECTING LOCALIZED ELECTRICAL SIGNALS AND PROVIDING ELECTRICAL STIMULATION

(75) Inventor: Walter G. Besio, Kingston, RI (US)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 13/361,452

(22) Filed: Jan. 30, 2012

(65) Prior Publication Data

US 2012/0150011 A1    Jun. 14, 2012

Related U.S. Application Data

(63) Continuation of application No. PCT/US2010/054211, filed on Oct. 27, 2010.

(60) Provisional application No. 61/255,635, filed on Oct. 28, 2009.

(51) Int. Cl.
*A61B 5/0478* (2006.01)
*A61N 1/04* (2006.01)
*A61B 5/0484* (2006.01)

(52) U.S. Cl. ........ 600/388; 600/383; 600/393; 600/544; 607/139

(58) Field of Classification Search .................. 600/382, 600/383, 393, 388, 389, 544, 545; 607/139
See application file for complete search history.

(56) References Cited

U.S. PATENT DOCUMENTS

| | | | | |
|---|---|---|---|---|
| 4,907,601 | A * | 3/1990 | Frick | 607/72 |
| 5,111,812 | A * | 5/1992 | Swanson et al. | 607/2 |
| 6,073,039 | A * | 6/2000 | Berson | 600/372 |
| 7,305,268 | B2 * | 12/2007 | Gliner et al. | 607/45 |
| 7,308,294 | B2 | 12/2007 | Hassonjee et al. | |
| 2003/0125786 | A1 * | 7/2003 | Gliner et al. | 607/116 |
| 2004/0088036 | A1 * | 5/2004 | Gilbert | 607/148 |
| 2004/0122336 | A1 * | 6/2004 | Jang et al. | 600/547 |
| 2004/0181141 | A1 * | 9/2004 | Kislov et al. | 600/393 |
| 2004/0199237 | A1 | 10/2004 | Mills et al. | |
| 2006/0173510 | A1 | 8/2006 | Besio et al. | |

FOREIGN PATENT DOCUMENTS

WO    2008005478 A2    1/2008

OTHER PUBLICATIONS

Lu et al. "Pasteless, Active, Concentric Ring Sensors for Directly Obtained Laplacian Cardiac Electrograms" Journal of Medical and Biological Engineering, 22(4): 199-203 (2002).*

(Continued)

*Primary Examiner* — Lee S Cohen
*Assistant Examiner* — Erin M Cardinal
(74) *Attorney, Agent, or Firm* — Gesmer Updegrove LLP

(57) ABSTRACT

A biomedical electrode is disclosed that includes at least first and second electrical nodes for connection to medical equipment. The biomedical electrode includes a first electrical node including a disc of conductive material having a diameter $d_1$, and a second electrical node including a ring of conductive material. The ring is concentric with the disc and has a diameter $d_2$ that is larger than $d_1$ and having a ring thickness $t_2$ such that $(4 \leq d_1/t_2 \leq 6)$.

18 Claims, 8 Drawing Sheets

OTHER PUBLICATIONS

Datta et al. "Transcranial current stimulation focality using disc and ring electrode configurations: FEM analysis" J. Neural Eng. 5: 163-174 (2008).*

International Preliminary Report on Patentability issued on May 10, 2012 in connection with PCT/US2010/054211, 16 pages.

International Search Report and Written Opinion issued on Feb. 8, 2011 in connection with International Application PCT/US2010/054211, 24 pages.

Ames, W.F., "Numerical Methods for Partial Differential Equations," Barnes & Noble, Inc., NY, 1969, cover page and pp. 15-19.

Besio, W., et al., "Analysis of Skin-Electrode Impedance Using Concentric Ring Electrode," Engineering in Medicine and Biology Society, 28th Annual International Conference of the IEEE, Aug. 30, 2006, pp. 6414-6417.

Besio, W., et al., "Application of Tripolar Concentric Electrodes and Prefeature Selection Algorithm for Brain-Computer Interface," IEEE Transactions on Neural Systems and Rehabilitation Engineering, Apr. 1, 2008, pp. 191-194.

Besio, W., et al., "Comparison of Bipolar vs. Tripolar Concentric Ring Electrode Laplacian Estimates," Annual International Conference of the IEEE Engineering in Medicine and Biology Proceedings—Conference Proceedings, Sep. 1, 2004, pp. 2255-2258.

Besio, W., et al., "Development of Tri-polar Concentric Ring Electrode for Acquiring Accurate Laplacian Body Surface Potentials," Annals of Biomedical Engineering, Mar. 2006, pp. 426-435.

Besio, W., et al., "Effects of Noninvasive Transcutaneous Electrical Stimulation Via Concentric Ring Electrodes on Pilocarpine-Induced Status Epilepticus in Rats," Epilepsia, Raven Press Ltd, Dec. 1, 2007, pp. 2273-2279.

Besio, W., et al., "Tri-Polar Concentric Ring Electrode Development for Laplacian Electroencephalography," IEEE Transactions on Biomedical Engineering, May 2006, pp. 926-933.

Besio, W., et al., "Tripolar Laplacian Electrocardiogram and Moment of Activiation Isochronal Mapping," Physiological Measurement, Institute of Physics Publishing, Bristol, GB, May 1, 2007, pp. 515-529.

Long-Stroke Spring-Loaded Pin Product (Product No. 0914), sold by Mill-Max Mfg. Corp. of Oyster Bay, New York, 1 page.

Cao, Y-Z, et al., "Surface Laplacian Approximation Theory of the Triple Concentric Electrode and Its Error Analysis," Tianjin Daxue Xuebao—Journal of Tianjin University, Mar. 1, 2006, pp. 360-364.

Chen, T., et al., "Computer Simulation Comparison of Tripolar, Bipolar, and Spline Laplacian Electrocadiogram Estimators," Engineering in Medicine and Biology Society, Annual International Conference of the IEEE, Sep. 3, 2009, pp. 3286-3289.

Conductive Yarns (sold under the brand name NOVONIC by W. Zimmermann GmbH & Co. of Germany), 11 pages.

Farina, D., et al., "Concentric-Ring Electrode Systems for Noninvasive Detection of Single Motor Unit Activity," IEEE, Transactions in Biomedical Engineering, Nov. 2001, pp. 1326-1334.

He, B., et al., "Body Surface Laplacian ECG Mapping," IEEE Transactions in Biomedical Engineering, 1992, pp. 1179-1191.

He, B., et al., "Body Surface Laplacian Mapping in Man," IEEE EMBS, 1991, pp. 784-786.

Huiskamp, G., "Difference Formulas for the Surface Laplacian on a Triangulated Surface," J. Computational Physics, 1991, pp. 477-496.

Koka, K., et al., "Improvement of Spatial Selectivity and Decrease of Mutual Information of Tri-Polar Concentric Ring Electrodes," Journal of Neuroscience Methods, Jun. 9, 2007, cover page and pp. 216-222.

Van Oosterom, A., et al., "Computer the Lead Field of Electrodes with Axial Symmetry," Medical & Biological Engineering & Computing, 1983, pp. 473-481.

Webster, J., "Medical Instrumentation Application and Design 3rd Ed.," John Wiley & Sons, Inc., 1998, cover page, preface, and pp. 183-263.

* cited by examiner

BIOMEDICAL ELECTRODE FOR DETECTING LOCALIZED ELECTRICAL SIGNALS AND PROVIDING ELECTRICAL STIMULATION

PRIORITY

This application is a continuation application of PCT/US2010/054211 filed on Oct. 27, 2010, which claims priority to U.S. Provisional Patent Application Ser. No. 61/255,635 filed Oct. 28, 2009, the entire disclosures of each of which are hereby incorporated by reference in their entirety.

BACKGROUND

The invention generally relates to biomedical electrodes and relates in particular to biomedical electrodes for detecting localized electrical signals within a subject as well as biomedical electrodes for providing electrical stimulation to a subject.

Conventional disc biomedical electrodes have generally changed little since Hans Berger first recorded the human electroencephalogram (EEG) in 1924. One drawback of conventional EEG methods that are recorded with disc electrodes, is that the procedure lacks high spatial resolution. This is primarily due to the blurring affects of the different conductivities of the volume conductor such as the cerebrospinal fluid, skull, and the scalp. Conventional EEG signals recorded with disc electrodes also have reference electrode problems as idealized references are not available with EEG. Placing the reference at different locations changes the characteristics of the EEG signals.

There are previous reports of concentric ring electrodes. Many such reports however, such as "Exploration du Champ Electrique Precordial a l'aide de deux Electrodes Circulaires, Concentrique et Rapproches" by V. Fattorusso and J. Tilmant, *Arch Mal du Coeur*, v. 42, pp 452-455 (1949); "Body Surface Laplacian Mapping in Man" by B. He and R. J. Cohen, *IEEE EMBS*, v. 13, no. 2, pp. 784-786 (1991); and "Computing the Lead Field of Electrodes with Axial Symmetry" by A. van Oosterom and J. Strackee, *Medical & Biological Engineering & Computing*, no. 21, pp. 473-481 (1983) only disclose bipolar concentric electrodes. The article "Concentric-Ring Electrode Systems For Non-Invasive Detection of Single Motor Unit Activity" by D. Farina and C. Cescon, *IEEE, Transactions in Biomedical Engineering*, v. 48, no. 11, pp. 1326-1334 (November 2001) describes various concentric electrodes with up to four rings, but there is no specific description of how the signals were acquired (for example including electronic connectivity) other than the fact that weights are employed. U.S. Patent Application Publication No. 2004/0199237 (to Mills et al.) discloses a method and device for testing whether an electrode is functioning properly by passing small currents between a ring and a disc electrode. U.S. Patent Application Publication No. 2003/0125786 (to Gliner et al.) describes a tripolar concentric electrode for implantable neurostimulation use.

To increase the spatial frequency and selectivity the surface Laplacian has been utilized. Concentric ring electrodes automatically estimate the surface Laplacian significantly better than by processing conventional EEG signals (see "Development of Tri-Polar Concentric Ring Electrode for Acquiring Accurate Laplacian Body Surface Potentials", by W. Besio, R. Aakula, K. Koka and W. Dai, *Annals of Biomedical Engineering*, Vol. 34, No. 3, March 2006) and significantly improves the signal-to-noise level in EEG applications, (see "Tri-Polar Concentric Ring Electrode Development for Laplacian Electroencephalography, by W. Besio, R. Aakula, K. Koka and W. Dai, *IEEE Transactions on Biomedical Engineering*, Vol. 53, No. 5, May 2006), as well as spatial selectivity, and mutual information (see "*Improvement of Spatial Selectivity and Decrease of Mutual Information of Tri-Polar Concentric Ring Electrodes*", by K. Koka and W. Besio, *Journal of Neuroscience Methods*, Vol. 165, pp. 216-222, Jun. 9, 2007). The reference problem is alleviated as well since bipolar differences are taken at closely spaced electrode elements.

Theory has shown that the elements of the electrodes should have equal area to prevent electrode offset potentials due to electrode half-cell potentials (see "Body Surface Laplacian ECG Mapping" by B. He and R. J. Cohen, *IEEE Transactions in Biomedical Engineering*, v. 39, no. 11, pp. 1179-1191 (1992); and "Medical Instrumentation Application and Design $3^{rd}$ ed." by J. Webster, John Wiley & Sons, Inc. (1998)). To use the finite difference approximation of the Laplacian described in "Numerical Methods for Partial Differential Equations" by W. F. Ames, Barnes & Noble, Inc., NY, pp. 15-19 (1969) and the methods of "Difference Formulas for the Surface Laplacian on a Triangular Surface" by G. Huiskamp, J. Computational Physics, v. 95, no. 1, pp. 477-496 (1991) to relate the finite difference method to a concentric ring electrode, the implied theory is that the center disc is a ring whose radius is equal to the ring and the outer ring is the same thickness as the ring of the disc. When the rings are of equal thickness the diameter of the central disc is twice the thickness of the outer ring. "Numerical Methods for Partial Differential Equations" by W. F. Ames, Barnes & Noble, Inc., NY, pp. 15-19 (1969) also states that the spacing between the rings, and disc, should be equal. For example, FIG. 1 shows a prior art concentric ring electrode 10 that includes a disc 12, an inner ring 14 a middle ring 16 and an outer ring 18. As discussed above, conventionally, the thickness of each ring is the same (t) and the diameter of the disc 12 is 2t. The spacing between the disc and each of the rings (which includes a dielectric material 8) is also conventionally t.

Further, an electrode gel (e.g., an electrolyte) has conventionally been used to bridge between electrodes and a cleaned surface of a subject (e.g., the scalp). The spacing required between electrodes may be so small that smearing of the electrolyte (and thus short circuiting of the bioelectric signal) may occur. Additionally, and perhaps most importantly, the application and removal of electrolyte gels is an unpleasant process for the subject, and time consuming for the clinician or care giver. There are also toxicological concerns with electrolyte gels where dermatological responses are common.

To avoid the problems of electrolytes, dry electrodes (not using a gel) have been introduced. With dry electrodes, however, movement artifacts are more prevalent due to the absence of a thick electrolyte layer (as is present in gels, which provides a shock absorber function). The introduction of active electrodes (where buffering/amplification takes place at the electrode site) provides much less emphasis on the skin-electrode impedance. An added concern with dry electrodes is that the large RC constant, which exists at the input of the unity gain amplifiers typically used for this application, prolongs the effect of large artifacts.

There is a need therefore, for an improved biomedical electrode that may be used without the current drawbacks yet may also provide consistent and reliable high resolution signals.

SUMMARY

In accordance with an embodiment, the invention provides a biomedical electrode that includes at least first and second electrical nodes for connection to medical equipment. The biomedical electrode includes a first electrical node including a disc of conductive material having a diameter $d_1$, and a second electrical node including a ring of conductive material. The ring is concentric with the disc and has a diameter $d_2$ that is larger than $d_1$ and having a ring thickness $t_2$ such that $(4 \leq d_1/t_2 \leq 6)$.

In accordance with another embodiment, the invention provides a biomedical electrode including at least first, second and third electrical nodes for connection to medical equipment. The first electrical node includes a disc of conductive material having a diameter $d_1$, the second electrical node includes a first ring of conductive material, wherein the first ring is concentric with the disc and has a diameter $d_2$ that is larger than $d_1$ and having a ring thickness $t_2$ such that $(4 \leq d_1/t_2 \leq 6)$. The third electrical node includes a second ring of conductive material, and the second ring is also concentric with the disc and has a diameter $d_3$ that is larger than $d_2$ and a ring thickness $t_3$ such that $(4 \leq d_1/t_3 \leq 6)$.

In accordance with a further embodiment, the invention provides a biomedical electrode including at least first, second, third and fourth electrical nodes for connection to medical equipment. The first electrical node includes a disc of conductive material having a diameter $d_1$. The second electrical node includes a first ring of conductive material, wherein the first ring is concentric with the disc and has a radius $\alpha$ that is larger than $d_1/2$. The third electrical node includes a second ring of conductive material, wherein the second ring is also concentric with the disc and has a radius $\beta$ that is larger than $d_2/2$. The fourth electrical node includes a third ring of conductive material, wherein the third ring is also concentric with the disc and has a radius of thirty millimeters that is larger than $d_3/2$, such that $(3\alpha\beta)^2$ is less than about $0.225 \text{ cm}^4$.

BRIEF DESCRIPTION OF THE ILLUSTRATED EMBODIMENTS

The following description may be further understood with reference to the accompanying drawings in which.

Figure 10:
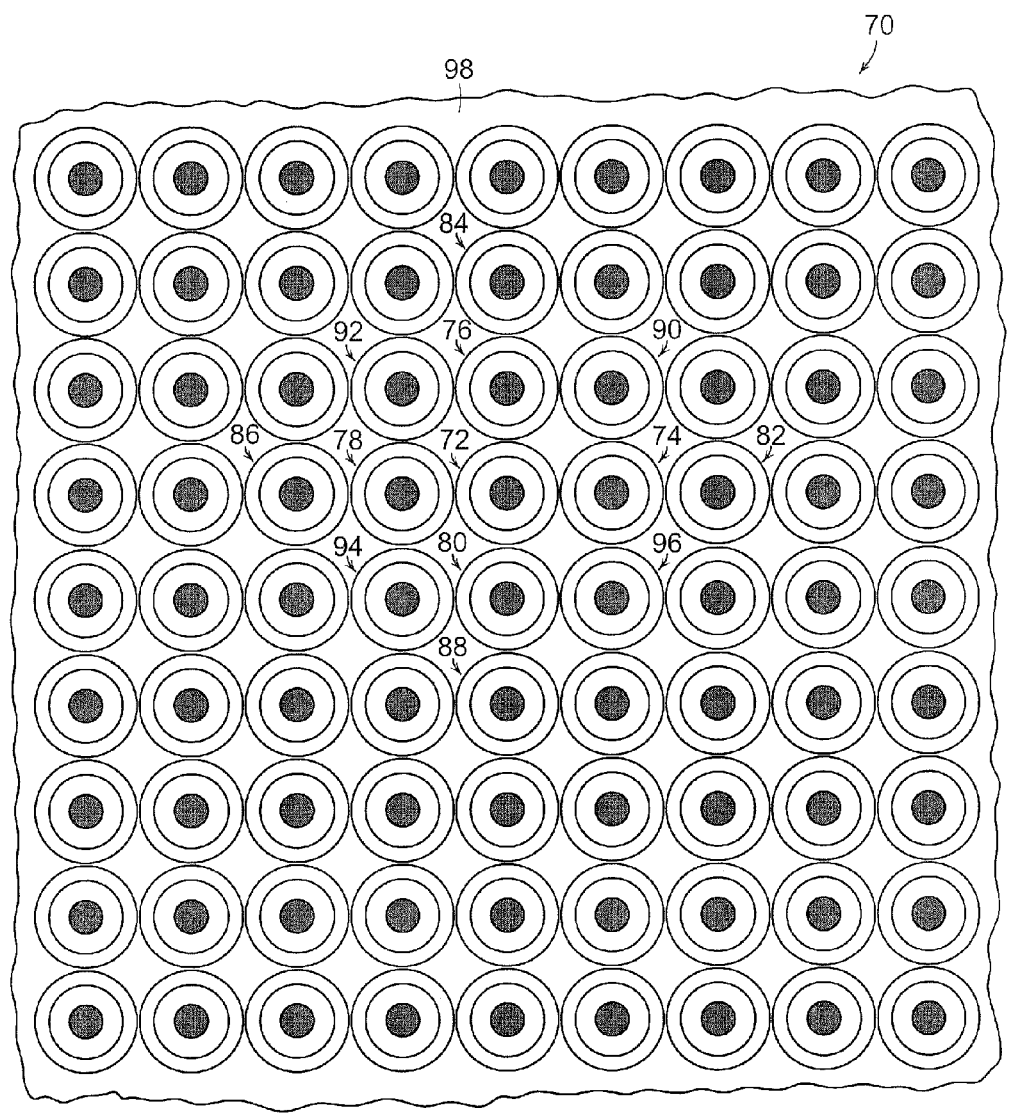
Figure 11:
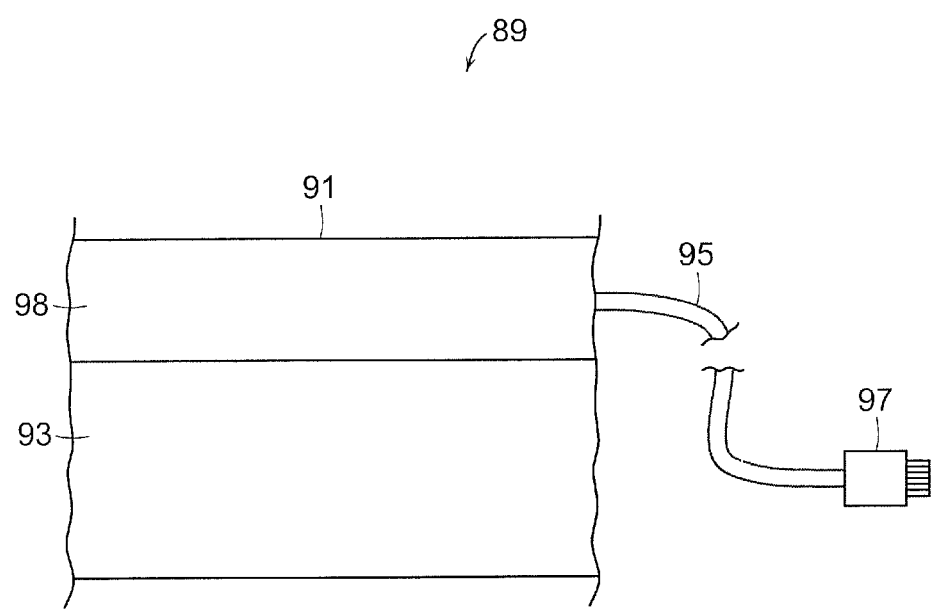
Figure 12:
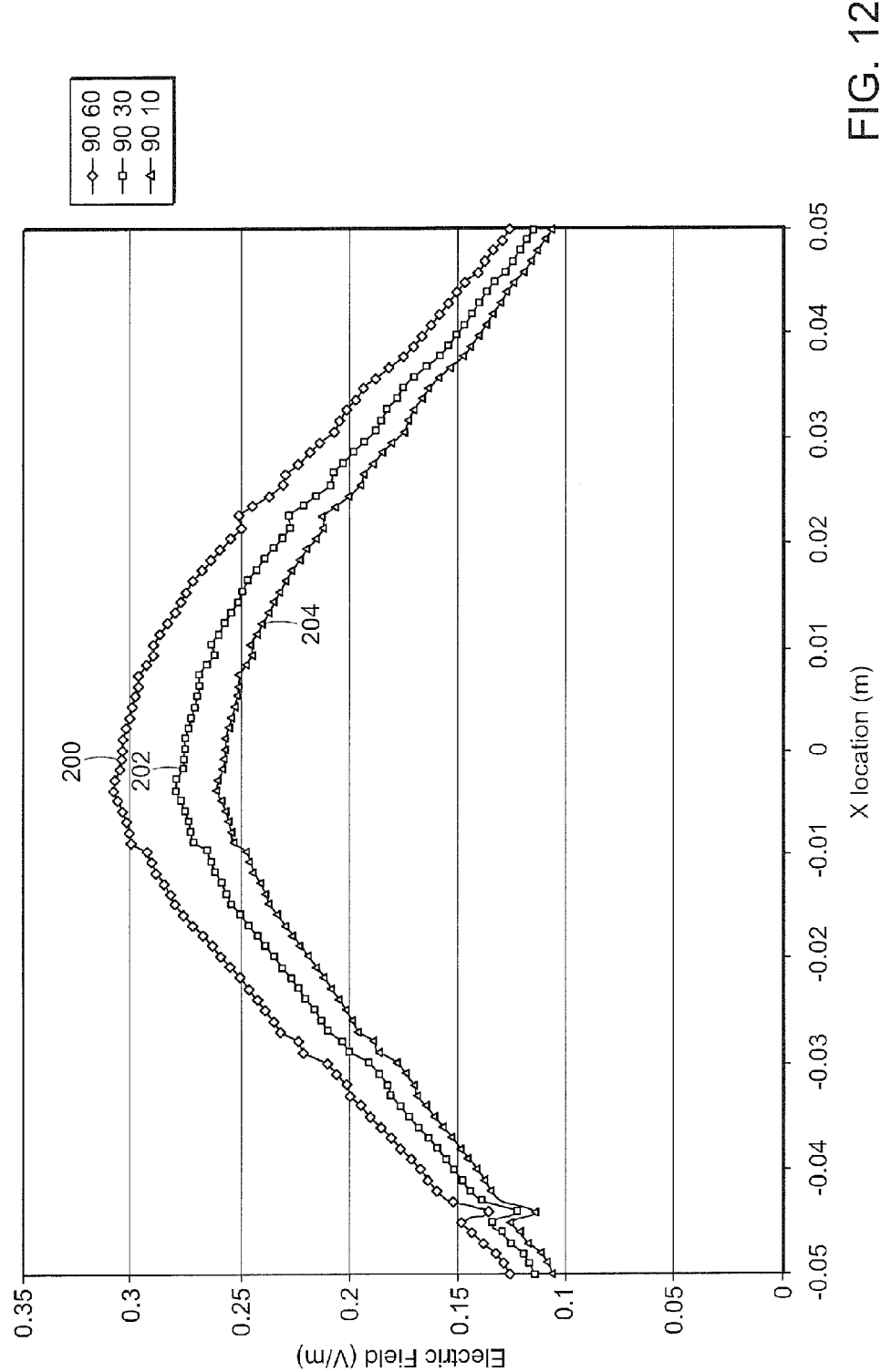

FIG. 10 shows an illustrative diagrammatic view of an array of electrodes of an embodiment of the present invention; and FIG. 11 shows an illustrative diagrammatic side view of an article including a fabric electrode in accordance with an embodiment of the invention; and FIG. 12 shows an illustrative diagrammatic view of electric field profiles extracted across an x-axis for three different stimulation currents.

The drawings are shown for illustrative purposes only.

DETAILED DESCRIPTION

It has been discovered that the diameters of the conductive discs and the thickness of conductive rings significantly impacts performance of biomedical electrodes. For example, suitable results were not achieved when concentric electrodes were used for stimulation with an outer ring having a diameter that is less than approximately 2.0 cm. Also, when the diameter of the inner disc is about two times the thickness of the outer ring, suitable results were not obtained.

Applicant has discovered that suitable electrodes should include an outer diameter of at least about 3.0 cm, and that the ratio of the center disc diameter to the outer ring thickness should be at least about four and less than about six, and preferably less than about five, with the ratio increasing for smaller diameter electrodes.

For a bipolar electrode therefore, if the outer ring thickness, is $t_2$ then the diameter of the inner ring $d_1$ should be $t_2$ multiplied by at least about four but less than about five $(4 \leq d_1/t_2 \leq 5)$. For example, for an electrode with an outer ring diameter of 16 mm and thickness of 1.0 mm the electrode works well if the diameter of the center disc is 4.0 mm. In another embodiment, when the outer ring diameter is 6.0 mm and thickness of 0.4 mm the electrode works well when the center disc diameter is 2.0 mm. The improvements gained with this ratio for stimulation also allow for high-fidelity signal acquisition as well.

Figure 1:
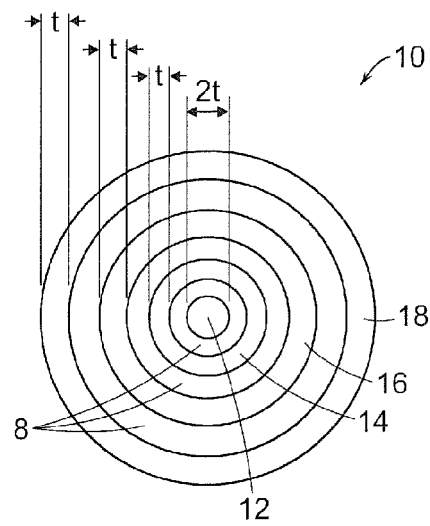
FIG. 1 shows an illustrative diagrammatic view of a prior art biomedical electrode.
Figure 2:
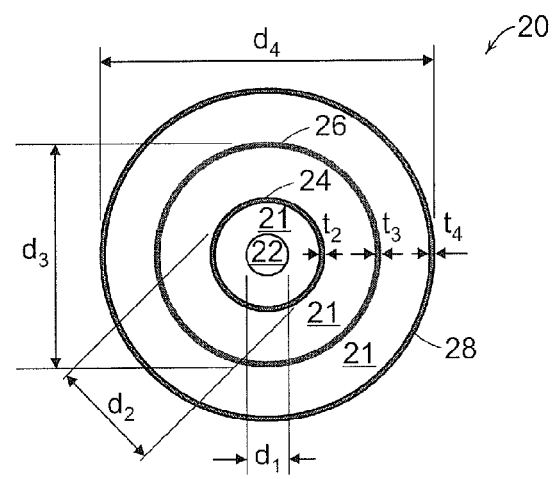
FIG. 2 shows an illustrative diagrammatic view of a biomedical electrode in accordance with an embodiment of the invention.

FIG. 2, for example, shows a quadra-polar biomedical electrode design in accordance with an embodiment of the invention. The biomedical electrode design 20 includes a center conductive ring 22, two concentric mid-conductive rings 24 and 26, and an outer concentric conductive ring 28. The inner ring has a diameter $d_1$ as shown, the rings 24 and 26 have diameters of $d_2$ and $d_3$ as shown, and the outer ring has a diameter $d_4$ as shown. The conductive rings 24, 26 and 28 each have ring thickness $t_2$, $t_3$ and $t_4$ as shown, and the diameters $d_2$, $d_3$ and $d_4$ are measured to the outer edge of each of the conductor thicknesses. In certain embodiments, $t_1 \geq t_2 \geq t_3$ and in an embodiment, $t_1 = t_2 = t_3$. A dielectric material is provided in the spaces 21 between the disc and rings as shown. The conductive material used for the rings may include silver/silver chloride, gold, tin etc.

It has also been discovered that the distance between the ring conductors affects performance as well, and that an optimal spacing that is contrary to the conventional approach provides surprising results. Mathematical analysis has shown that there are certain gap sizes that provide the most accurate approximation to the Laplacian. For this theoretical exercise, three rings concentric to a central disc were used in a quadra-polar concentric ring configuration as shown in FIG. 2. The outer ring diameter was fixed and the two middle rings were allowed to be adjusted to minimize the error approximating the Laplacian. The first ring 24 radius $(d_2/2)$ was constrained to be greater than the radius of the central disc 22 $(d_1/2)$ but less than the radius of the outermost ring 28 $(d_4/2)$ and the radius of the second ring 26 $(d_3/2)$. The radius of the second ring 26 ($d_3/2$) was greater than the radius of the first ring 24 ($d_1/2$) but less than the radius of the outer ring 28 ($d_4/2$).

Figure 4:
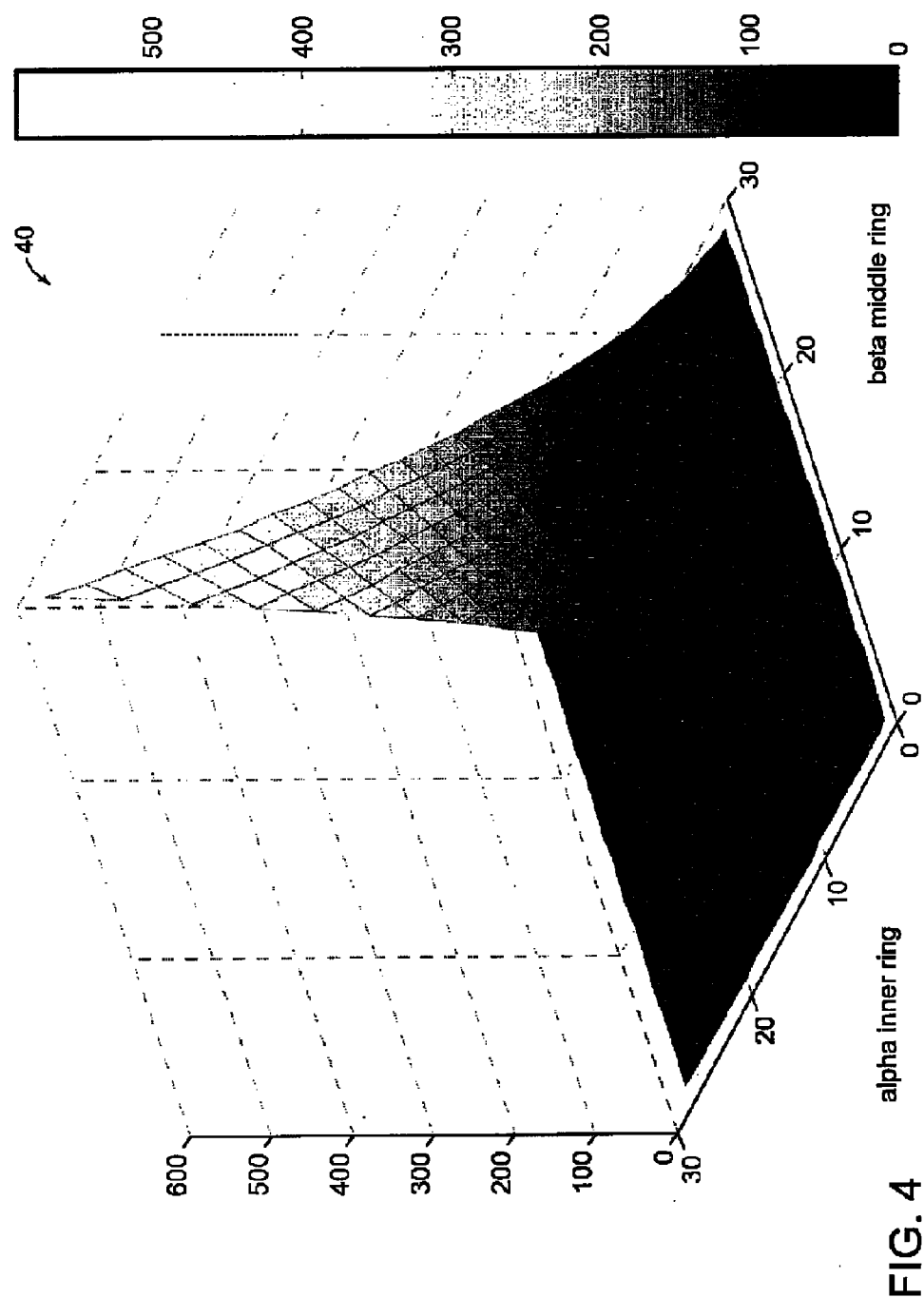
FIG. 4 shows a graphical illustration of the relationship between first and second ring radii of the quadra-polar layout of FIG. 2 and the associated error approximating the Laplacian where the diameter of the outermost ring is set to thirty millimeters.

It has been found that there are ranges of radii for each ring that minimize the error approximating the Laplacian. For example, if the first ring 24 radius is α and the radius of the second ring 26 is β, and if the outer ring radius is fixed at 3.0 (arbitrary units) then the optimal radii for the electrode are the points where the function $(3\alpha\beta)^2$ is minimized. FIG. 4 shows for example, at 40 a relationship between the error approximating the Laplacian as a function of the radius of a first inner ring 24 and the radius of a second inner ring 26 when the radius of the outermost ring 28 is fixed to 30.0 mm. If α=3.0 mm and β=5.0 mm, with the outer radius fixed to 30.0 mm, the above function yields 202,500 mm$^4$, or 0.2025 cm$^4$. Preferably, the function yields less than about 0.225 cm$^4$.

Assuming an outer ring diameter of 30 mm and that the ring thicknesses of all the rings is 1.0 mm then the center disc diameter would be 2.0 mm. The radius at the center of the first ring could vary from 1.5 mm to 14 mm and the second ring radius at the center could vary from 2.5 mm to 14 mm. To minimize the error approximating the Laplacian if β is kept large, say at 13 mm, then α must be small, e.g., 4.0 mm. Keeping the radius of the first inner ring 24 and the radius of the second inner ring 26 both small is preferred such as $d_2$=6.0 mm and $d_3$=10.0 mm. When not maximizing the approximation to the Laplacian, the insulating gaps may be proportioned equally.

Electrodes of the invention may be used for the acquisition of biopotentials in clinical and research applications. The new electrodes may be used for recording the electroencephalogram (EEG), electrocardiogram (ECG), electromyogram (EMG), electrooculogram (EOG) etc. Use of the electrodes is also not limited to noninvasive recording; as they may also be used as implantable electrodes. They could also be used in any application where potentials need to be measured on a non-biological surface where movement artifact suppression is beneficial. Concentric electrodes take the differences of signals that are impressed on electrode elements very closely spaced (for EEG typically within 1.0 mm or less). The interference is nearly the same on both elements of the electrode and is automatically cancelled by common mode rejection. It may further be possible that electrodes of the invention are used in an application that permits or requires that a subject be mobile while monitoring their bio-potentials.

Figure 3:
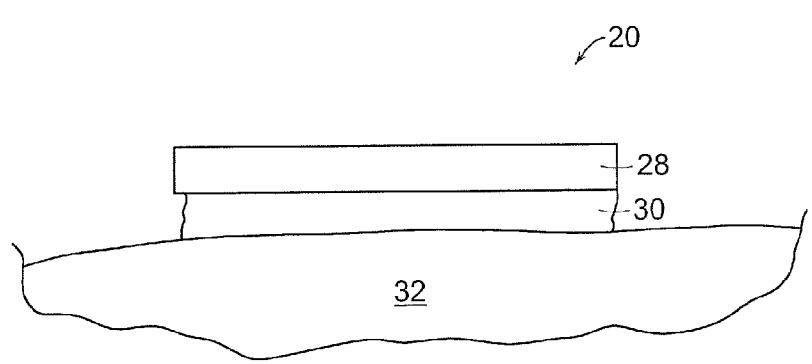
FIG. 3 shows an illustrative diagrammatic side view of the biomedical electrode of FIG. 2 applied to a subject.

A biomedical electrode of the invention may include conductive rings that themselves contact a patient's skin either with or without the use of a hydrogel. For example, FIG. 3 shows a side view of the biomedical electrode 20 as applied to a patient 32 using an electrolytic gel 30. In various embodiments, different electrically conductive elements (22, 24, 26, 28) may be coupled together. In an embodiment for example, the central disc 22 and the outermost ring 28 may be coupled together and to ground.

For example, electrodes of tri-polar biomedical electrodes of various embodiments may have the following dimensions as shown in Table 1 below.

TABLE 1

| TYPE (Dia.) | central disc radius | 1$^{st}$ ring inner radius | 1$^{st}$ ring outer radius | 2$^{nd}$ ring inner radius | 2$^{nd}$ ring outer radius |
| --- | --- | --- | --- | --- | --- |
| 0.6 cm | 1.0 mm | 1.6 mm | 2.0 mm | 2.6 mm | 3.0 mm |
| 1.0 cm | 1.4 mm | 2.6 mm | 3.2 mm | 4.4 mm | 5.0 mm |
| 1.6 cm | 2.0 mm | 3.0 mm | 4.0 mm | 7.0 mm | 8.0 mm |

Analyses of the electrode element ratios for these are as shown in Table 2 below.

TABLE 2

| Electrode Dia. (cm) | disc dia. (mm) | outer ring thickness (mm) | dd/orw ratio |
| --- | --- | --- | --- |
| 0.6 | 2.0 | 0.4 | 5 |
| 1.0 | 2.8 | 0.6 | 4.67 |
| 1.6 | 4.0 | 1.0 | 4 |

The electrode element areas are shown in Table 3 below.

TABLE 3

| Electrode Dia. (cm) | disc (mm$^2$) | mid ring (mm$^2$) | outer ring (mm$^2$) |
| --- | --- | --- | --- |
| 0.6 | 3.1 | 4.5 | 7.0 |
| 1.0 | 6.2 | 10.9 | 17.7 |
| 1.6 | 12.6 | 22.0 | 47.1 |

For the above calculations for the electrode having an electrode outer diameter of 0.6 cm, the disc has a diameter of 2.0 mm, a disc radius of 1.0 mm, a disc area of 3.14 mm$^2$, a first ring inner radius of 1.6 mm, a first ring outer radius of 2.0 mm, a first ring area of 4.52 mm$^2$, a second ring inner radius of 2.6 mm, a second ring outer radius of 3.0 mm, and a second ring area of 7.04 mm$^2$. For the electrode having an electrode outer diameter of 1.0 cm, the disc has a diameter of 2.8 mm, a disc radius of 1.4 mm, a disc area of 6.16 mm$^2$, a first ring inner radius of 2.6 mm, a first ring outer radius of 3.2 mm, a first ring area of 10.93 mm$^2$, a second ring inner radius of 4.4 mm, a second ring outer radius of 5.0 mm, and a second ring area of 17.72 mm$^2$. For the electrode having an electrode outer diameter of 1.6 cm, the disc has a diameter of 4.0 mm, a disc radius of 2.0 mm, a disc area of 12.57 mm$^2$, a first ring inner radius of 3. mm, a first ring outer radius of 4.0 mm, a first ring area of 21.99 mm$^2$, a second ring inner radius of 7.0 mm, a second ring outer radius of 8.0 mm, and a second ring area of 47.12 mm$^2$.

Figure 5:
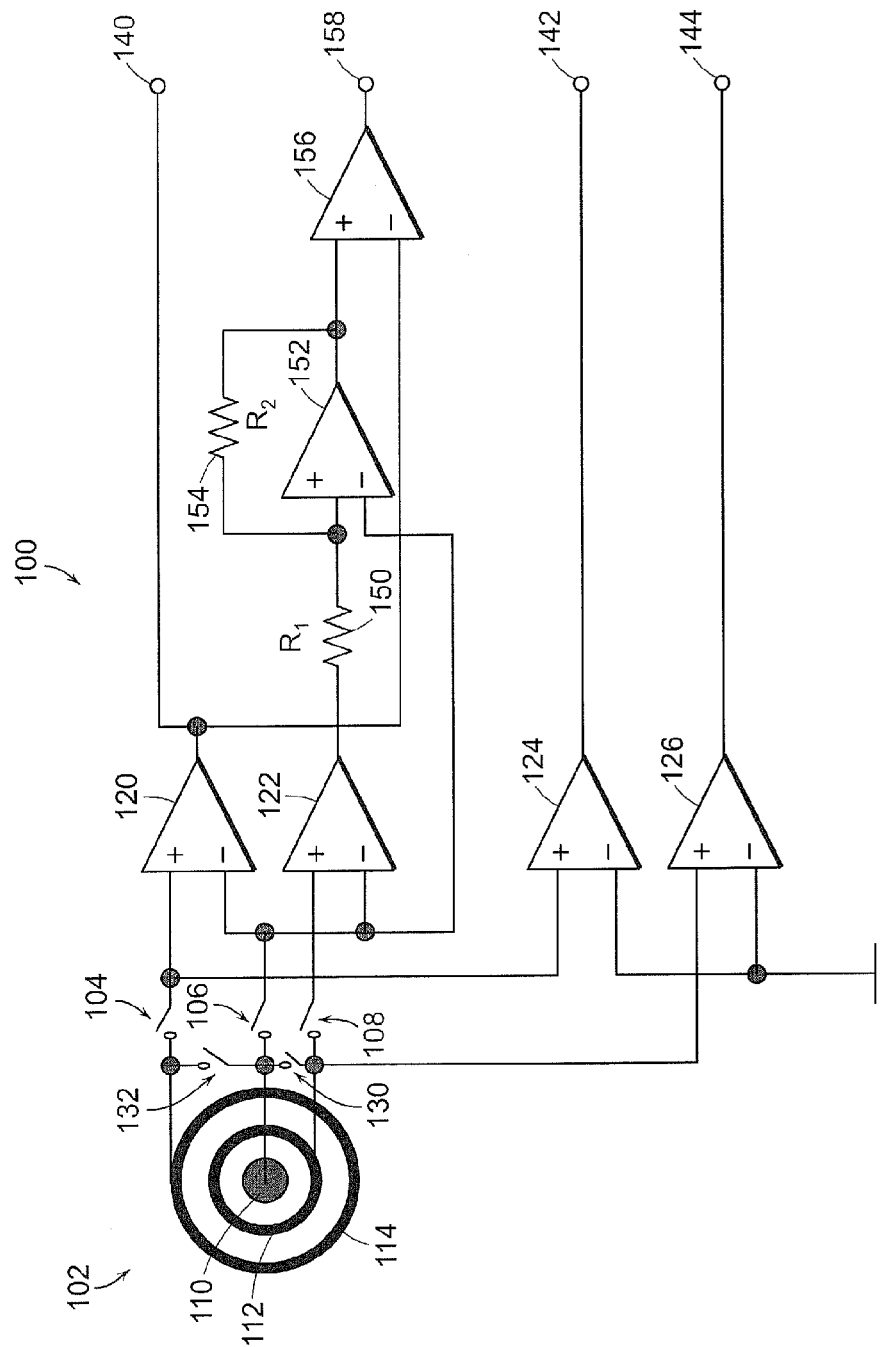
FIG. 5 shows an illustrative diagrammatic view of a multiple output electronic circuit for use with a biomedical electrode in accordance with an embodiment of the invention.

FIG. 5 shows a switching circuit system 100 for communicating with an electrode in accordance with an embodiment of the invention that provides for multiple outputs. In particular, the quad output concentric electrode 102 simultaneously provides two forms of unipolar, a bipolar output, as well as tripolar output using a series of switches 104, 106, and 108 that selectively couple the inner conductor 110, a middle conductor 112 and an outer conductor 114 to amplifiers 120, 122, 124 and 126 as shown. The system also includes switches 130 and 132 for selectively coupling the center conductor 110 to either the middle conductor 112 or the outer conductor 114 respectively or both.

The amplifier 120 receives its positive input from the outer conductor 114 and its negative input from the center conductor 110, and the output of the amplifier 120 provides a bipolar output signal 140. The amplifier 124 receives its positive input from the outer conductor 114 and its negative input is coupled to ground. The output of the amplifier 124 provides an outer ring monopolar output signal 142 when the switch 132 is open and the switch 104 is closed. The amplifier 126 receives its positive input from the middle conductor 112 and 114 and its negative input is coupled to ground. The output of the amplifier 126 provides a switched monopolar output signal 144 when switches 130 and 132 are closed. Switches 104, 106 and 108 should be opened with the inputs to amplifiers 120, 122 and 124 connected to a reference or to a sample and hold circuit while, switches 130 and 132 are shorted. The amplifier 122 receives its positive input from the middle conductor 112 (via switch 108) and receives its negative input from the inner conductor 110 (via switch 106). The output of the amplifier 122 is provided to a positive input of a further amplifier 152 via a resistor 150 (R1 of e.g., 1 k Ohm) and the negative input of the amplifier 152 is coupled to the inner conductor 110. The output of the amplifier 152 is feedback coupled to the positive input through a resistor 154 (R2 of e.g., 16 k Ohm) and is also coupled to the positive input of a further amplifier 156. The negative input of the amplifier 156 is coupled to the output of the amplifier 120, and the output of the amplifier 156 provides a tripolar output signal (16(M−D)−(O−D)), where "M" is the middle ring potential, "D" is the disc potential, and "O" is the outer ring potential.

The outputs differ in spatial selectivity. This system produces a surface Laplacian output by taking the second radial spatial derivative of the surface signals and providing two forms of virtual unipolar output signals. The Laplacian operator is commonly performed in software to localize cortical activity since it approximates underlying cortical potentials from scalp voltage distributions. However, there may be circumstances when the tripolar concentric ring electrodes (TCRE)'s high spatial selectivity might also limit its utility, such as source reconstruction. The rationale for the proposed quad output concentric electrode is that it will maintain compatibility with existing EEG electrode methods, while also providing outputs with improved spatial localization of cortical activity. The spatial derivative outputs are self-referential, unlike unipolar electrodes, and are potentially less sensitive to most EEG artifacts. The above applies to EEG signals but is also appropriate for ECG, EMG, EOG, and other signal recordings.

Figure 6:
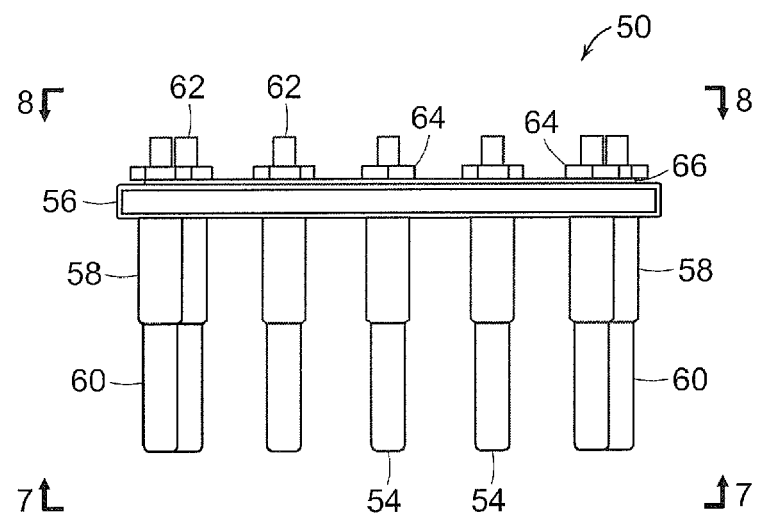
FIG. 6 shows an illustrative diagrammatic view of a biomedical electrode in accordance with another embodiment of the invention

FIG. 6 shows a biomedical electrode 50 in accordance with another embodiment of the invention. The biomedical electrode 50 in accordance with an embodiment includes a plurality of protruding electrodes 54 that extend through and protrude from a common base 56. Each electrode includes a fixed protruding portion 58 and a resilient protruding portion 60 that extends from the fixed protruding portion 58 as further shown in FIG. 6. As further shown in FIG. 8 (which shows a top view), each electrode also includes a mounting post 62 that extends through the base 56. Each mounting post 62 is threaded, and a nut 64 is used to fasten each electrode onto the base 56 as further shown in FIG. 9. In accordance with further embodiments, each protruding electrode may be attached to the base by a variety of known techniques, including for example, using solder, glue and/or press fit insertion.

Figure 8:
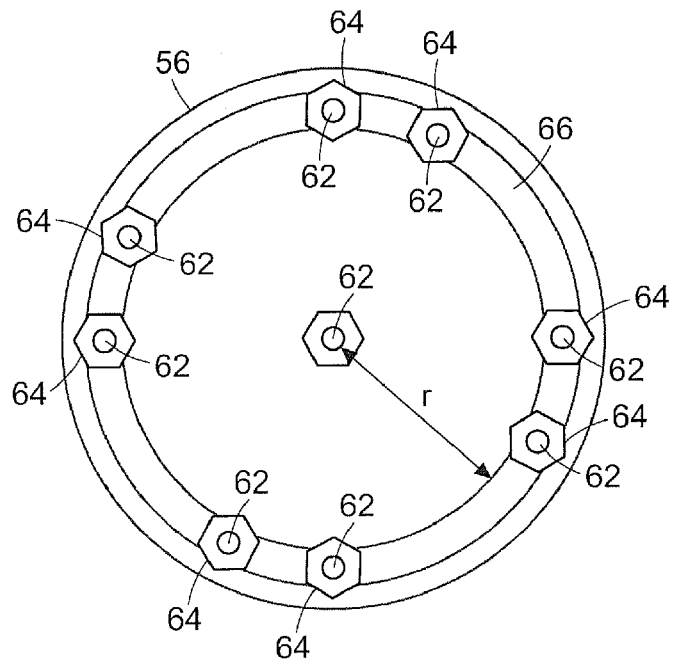
FIG. 8 shows an illustrative diagrammatic top view of the biomedical electrode of FIG. 6 taken along line 8-8 thereof.
Figure 9:
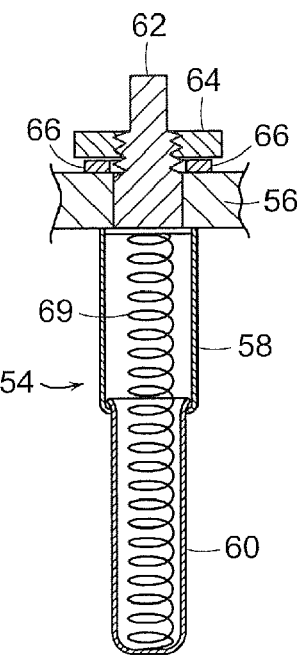
FIG. 9 shows an illustrative diagrammatic cross-sectional view of one protruding electrode in the biomedical sensor of FIG. 6.

In accordance with various embodiments the protruding electrodes 54 may be connected to monitoring equipment in such a way that they remain electrically independent of one another, or in some embodiments, one or more groups of electrodes may be commonly coupled via conductors. For example, FIG. 8 shows a first outer conductor 66 that electrically joins together the outer ring of electrodes. A second conductor may similarly electrically joins together an inner ring of electrodes. The innermost electrode (separated from the first outer conductor 66 by a distance r) is electrically independent of the others. Each conductor (e.g., 66) is coupled to its associated electrode 54 by being captured between the conductive fastening nut and the base 56 as shown in FIG. 9. Each electrode, therefore, is electrically conductive from the post 62, through the fixed and resilient protrusion sections 58 and 60. In accordance with further embodiments an electrically conductive material may also be included within each electrode to further enhance the electrical conductivity of each electrode. Each conductive ring may have any number of protruding electrodes. For example, the inner ring may have one electrode, the first ring may have six electrodes, the second ring may have nine electrodes, and the third (outermost) ring may have nine electrodes.

Figure 7:
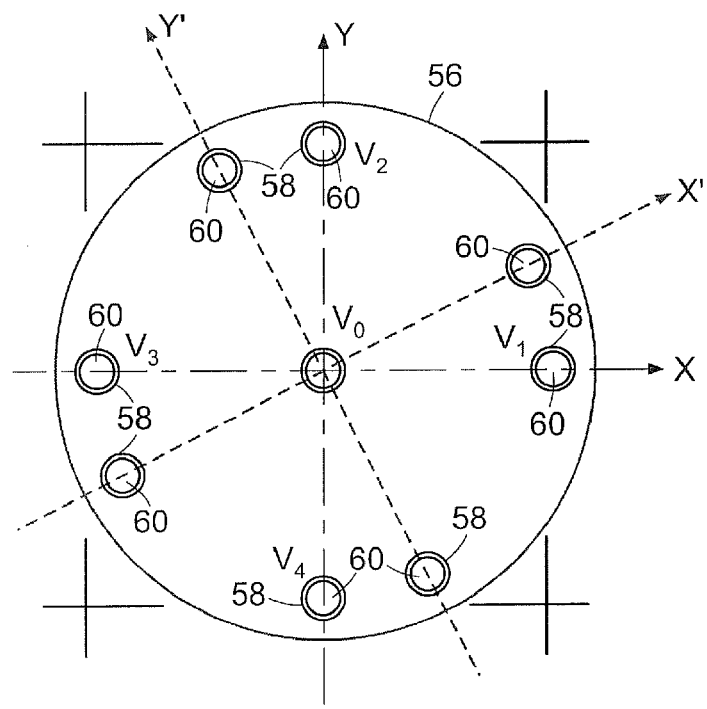
FIG. 7 shows an illustrative diagrammatic bottom view of the biomedical electrode of FIG. 6 taken along line 7-7 thereof.

With reference again to FIG. 7, the electrodes may be positioned at a plurality of locations along the outer conductor. For example, four electrodes may be positioned along the X and Y axes as shown, and additional electrodes may be positioned that are rotationally displaced from the X and Y axes such as on the X' and Y' axes as shown. The spacing between electrodes coupled to a common conductor may vary as long as sufficient contact is made with the patient through the protruding electrodes 54.

The fixed and resilient protruding portions may pass through the hair on a subject, and the biomedical sensors of the invention may be used either with or without a gel. The individual electrodes, in accordance with an embodiment, are shaped of tubular rods such that the resilient protruding portion 60 penetrates through hair reaching the scalp of a subject. With reference as well to FIG. 9, there is force exerted on the resilient protruding portion, from inside the fixed protruding portion, keeping the electrode 54 in contact with the patient. This force may be provided by a spring 69 in accordance with an embodiment. In further embodiments, such a force may be provided by any of a variety of techniques such as the use of pneumatic or hydraulic pressure within the protruding electrodes 54. In certain embodiments, spring loaded electrical connector pins such as the long-stroke spring-loaded pin product (product number 0914), sold by Mill-Max Mfg. Corp. of Oyster Bay, N.Y. may be used.

Another benefit of making the biomedical sensor out of independent protruding electrodes is that the force will keep the individual electrodes contacting the scalp even if the scalp is not flat. The electrodes 60 will follow the contour of the scalp or other body part to which the electrode is applied. Conversely, with a conventional solid ring, if there is a protrusion the ring may be raised up, not touching the scalp, altering the skin-to-electrode impedance. If a muscle contracts for example, protruding the skin upward below the surface of a conventional disc electrode, then part of the electrode may lose contact with the skin surface altering the skin-to-electrode impedance causing an artifact. Adding active electronics directly to the electrode matches the skin-to-electrode impedance better, permitting low impedance signals to be transmitted via wires to avoid AC power line interference. A conventional electrolytic gel may also be used to facilitate electrical conductivity with the subject.

During movements of the subject, therefore, the force on the electrodes will keep them in contact with the skin limiting signal loss or distortion from movement artifacts. As the shape of the skin changes, the independent elements automatically reshape to conform to the contour, retaining contact, reducing signal loss or distortion. In accordance with certain embodiments, a gel may be applied through the resilient protruding portion in accordance with an embodiment. Connecting the electrodes together in such a way as to provide effective concentric ring electrodes and/or virtual concentric ring electrodes may be employed to achieve significantly better signal to noise ratios, spatial selectivity, approximation of the Laplacian, and mutual information, i.e., signals from areas of the subject that are outside of the target area of interest below the sensor. The virtual concentric electrodes would automatically attenuate distant sources such as eye blinks, jaw movements, ECG and ballistic ECG. Electrode preparation time will also be significantly improved.

To make the flat-type electrodes so that they conform to the skin surface typically a skin-to-electrode paste is used. The paste has three functions: (1) matching skin-to-electrode impedance, (2) holding the electrode in place, and (3) acting as a shock absorber to lessen mechanical vibrations. With a dense array of electrodes (e.g., 64 or more), it may be advantageous to use a cap, or some other type of electrode fixation device, to hold the electrodes on the scalp or other skin surface. Under these circumstances it would be difficult to apply the paste and be certain the paste and electrode are making good contact with the scalp or skin. To overcome this obstacle a fabric type of electrode may be used.

In accordance with a further embodiment therefore, an array of biomedical electrodes 70 may be provided in a fabric 98 of a garment 89 (shown in FIG. 11) as fabric electrodes as shown in FIG. 10. The garment 89 also includes a support fabric 93 on the surface of the fabric electrodes opposite the subject contact surface 91 of the electrode as further shown in FIG. 11. The electrodes may be coupled to monitoring equipment via a connector 97 attached to the electrodes 70 via a connector cable 95.

The fabric could be made of conductive yarns that take the shape of the electrodes. If the yarn has branches or protruding hairs the conductive yarns could help bridge through hair to connect the electrode to the scalp or skin. A liquid gel could also be applied to the fabric electrode that would help wet the hair and make contact with the scalp or skin. It is known that metallic conductors could be inserted into yarns to make the yarns conductive. It is also known that yarns may be soaked in carbon nanotube solutions to make the yarns conductive. Carbon foams, or other types of conductive foams, could also be used that would help bridge the gap and provide a shock absorber effect. Attaching the electrodes, whether fabric or other composition, could be accomplished with electrically conductive tape, such as ARcare® 8881 and ARcare® 90366 adhesive products sold by Adhesives Research, Inc. of Glen Rock, Pa. This type of attachment may be advantageous for stabilizing the skin-to-electrode contact.

The fabric 98 may, for example, include conductive yarns (e.g., as sold under the brand name NOVONIC by W. Zimmermann GmbH & Co. of Germany) that may be used for data transfer and/or power transfer (as well as textile-based heating). In particular, the conductive yarns may include a flexible core to ensure sufficient mechanical stability combined with high flexibility, wires that are shaped as a spiral to provide stretch resistance of the electrical conductor, and an outer textile to protect against overstretching and abrasion. In accordance with further embodiments, the garment may include textile-based electrodes as disclosed, for example, in U.S. Pat. No. 7,308,294. The textile interface (97) may be a NOVONIC a textile interface between electronics and textiles, which provides integration of sensors and communication in washable textiles.

The array of electrodes 70 includes biomedical electrodes 72, 74, 76, 78, 80, 82, 84, 86, 88, 90, 92, 94, 96 as disclosed in the above embodiments. In particular, the electrodes 72-96 each have a central disc and two concentric outer rings. For a particular application, for example, a five point configuration may be employed using electrodes 72-80. In particular, electrode 72 provides a central node, while electrodes 74-80 provide a ring.

For the five point configuration using bipolar electrodes the potentials from the outer ring and disc difference (outer ring potential–disc potential) of each of the five electrodes, would be combined using the following formula by Hjorth:

$$V_{FPM} = (V_{72} - V_{74}) + (V_{72} - V_{76}) + (V_{72} - V_{78}) + (V_{72} - V_{80})$$

Where $V_{FPM}$ is the estimate of the Laplacian at the center of the central electrode who's potential is $V_{72}$ and $V_{74}$-$V_{80}$ are the potentials of electrodes 74-80 respectively. The potentials $V_{72}$-$V_{80}$ would be the Laplacian estimates that are recorded from bipolar electrodes (outer ring potential–disc potential) or if using tripolar concentric ring electrodes $V_{72}$-$V_{80}$ would each be 16*(middle ring potential–disc potential)–(outer ring potential–disc potential) for each of the 5 electrodes. This could also be extended to nine points as well using the following relationships:

$$V_{NPM} = 16*[(V_{74}-V_{72})+(V_{76}-V_{72})+(V_{78}-V_{72})+(V_{80}-V_{72})] - [(V_{82}-V_{72})+(V_{84}-V_{72})+(V_{86}-V_{72})+(V_{88}-V_{72})]$$

where $V_{72}$–$V_{88}$ are either the bipolar or tripolar Laplacian potential estimates at electrodes 72-88. In accordance with other embodiments, electrodes 72-88 could be of other configurations having more or less rings and using other Laplacian estimation algorithms.

For stimulation, an array of electrodes could be used and stimulation could be targeted by using a subset of the electrodes such as electrodes 72-80 to reach a deeper central location than with just electrode 72. The electrodes 72-80 could be used to penetrate even deeper, and electrodes 72-96 to go deeper yet with less stimulation intensity on each electrode but covering a larger area.

If short the elements of the electrodes were shorted to make a disc, or virtual disc of electrodes, then the stimulation depth and area stimulated may be adjusted by using similar configurations only the center virtual disc electrodes will form one concentric electrode element, such as 72, and the surrounding virtual disc electrodes will form the outer ring, such as 74-80.

With a single tripolar electrode the stimulation depth, and volume of tissue, assuming stimulation intensity remains the same, can be adjusted by changing the diameter of the outer ring. However, the spatial resolution of where the stimulation is directed decreases inversely to the outer ring radius. To recover the fine depth of stimulation with a larger radius outer ring, stimulation can also be applied to the middle ring such as applying potential to a grid of a tube. This method has been tested with computer and physical models. The computer model was of four concentric spheres with different conductivities for the brain, cerebrospinal fluid (CSF), skull, and scalp. For instance, if the current applied through the outer ring of a 20 mm diameter tri-polar concentric electrode was 90 mA the depth of activation could be fine tuned by adjusting the current on the middle electrode. FIG. 12 shows the electric field profiles extracted across the x-axis of the model 49 mm into the brain generated from stimulation with the 20 mm diameter tri-polar concentric ring electrode. By keeping the outer ring stimulation current constant at 90 mA and changing the currents applied to the inner ring to 60 mA (shown at 200), 30 mA (shown at 202), and 10 mA (shown at 204) results in the electric field profiles shown in FIG. 12. The peak electric field values at a depth of 49 mm into the brain region of the model produced from stimulation with the electrode varied between 303 µV/mm and 256 µV/mm.

The magnitudes of the electric field (µV/mm) produced from stimulation with the 20 mm diameter tri-polar electrode at different depths in the brain layer of the model along the z-axis are presented in Table 4. The values other than those for the 77 mm (center) are of sufficient magnitude to provide neuronal modulation.

TABLE 4

| Input Stimulus (mA) (Outer/Middle) | 10 mm | 20 mm | 30 mm | 40 mm | 77 mm (center) |
|---|---|---|---|---|---|
| 90/60 | 5467 | 2002 | 938 | 489 | 90 |
| 90/30 | 4937 | 1813 | 851 | 443 | 82 |
| 90/10 | 4504 | 1687 | 792 | 413 | 76 |

Further implementation details and combinations of electrodes and conductive areas of electrodes are disclosed, for example, in U.S. Published Patent Application Publication No. 2006/0173510, the disclosure of which is hereby incorporated by reference in its entirety.

Those skilled in the art will appreciate that numerous modifications and variations may be made to the above disclosed embodiments without departing from the spirit and scope of the invention.

What is claimed is:

1. An array of biomedical electrodes, each biomedical electrode providing at least first and second electrical nodes for connection to medical equipment, said biomedical electrode comprising a first electrical node including a disc of conductive material having a diameter $d_1$, and at least three rings of conductive material, said at least three rings including a first ring and an outermost ring, said first ring providing a second electrical node and being concentric with the disc and having a diameter $d_2$ that is larger than $d_1$, said outermost ring being concentric with the disc and having a ring thickness $t_2$ such that ($4 \leq d_1/t_2 \leq 6$), each of said at least three rings being coupled to a switching network, and said outermost ring having a diameter of at least 3 cm, wherein a subset of said array of biomedical electrodes is employed for stimulation as well as sensing using said switching network.

2. The array of biomedical electrodes as claimed in claim 1, wherein each said biomedical electrode further includes a plurality of protruding electrodes, at least one of which extends from the disc of conductive material that is coupled to the first electrical node, and at least two of which extend from the first ring and are coupled to the second electrical node.

3. The array of biomedical electrodes as claimed in claim 1, wherein each of the plurality of at least 3 rings has the same ring thickness.

4. The array of biomedical electrodes as claimed in claim 1, wherein said switching network provides unipolar, bipolar and tripolar outputs for each biomedical electrode.

5. An array of biomedical electrodes, each biomedical electrode providing at least first, second and third electrical nodes for connection to medical equipment, said biomedical electrode comprising:
said first electrical node including a disc of conductive material having a diameter $d_1$;
said second electrical node including a first ring of conductive material, said first ring being concentric with the disc and having a diameter $d_2$ that is larger than $d_1$ and having a ring thickness $t_2$ such that ($4 \leq d_1/t_2 \leq 6$); and
said third electrical node including a second ring of conductive material, said second ring also being concentric with the disc and having a diameter $d_3$ that is larger than $d_2$ and having a ring thickness $t_3$ such that ($4 \leq d_1/t_3 \leq 6$), said nodes coupled to a switching circuit for selectively measuring a plurality of different electric potentials among the first electrical node, the second electrical node and the third electrical node, wherein a subset of said array of biomedical electrodes is employed for stimulation as well as sensing using said switching circuit, and wherein said switching circuit provides unipolar, bipolar and tripolar outputs for each biomedical electrode.

6. The biomedical electrode as claimed in claim 5, wherein said first and third electrical nodes are coupled together.

7. The biomedical electrode as claimed in claim 5, wherein $t_2 \geq t_3$.

8. The biomedical electrode as claimed in claim 7, wherein $t_2 = t_3$.

9. The biomedical electrode as claimed in claim 8, wherein said biomedical electrode further includes a fourth electrical node that includes a third ring of conductive material, said third ring being concentric with the disc and having a diameter $d_4$ that is larger than $d_2$ and having a ring thickness $t_4$ such that ($4 \leq d_1/t_4 \leq 6$).

10. The biomedical electrode as claimed in claim 5, wherein said biomedical electrode further includes a plurality of protruding electrodes that extend from a common base, at least one of said protruding electrodes being coupled to the first electrical node, at least two of said protruding electrodes being coupled to the second electrical node, and at least two of said protruding electrodes being coupled to the third electrical node.

11. A method of providing stimulation using the array of biomedical electrodes as claimed in claim 5, wherein said method includes steps of varying a stimulation current to reach varying depths within a subject, and providing the stimulation current to the subject.

12. The method as claimed in claim 11, wherein said step of varying the stimulation current involves varying a stimulation current applied to an inner conductive ring of a tri-polar electrode.

13. A biomedical electrode providing at least first, second, third and fourth electrical nodes for connection to medical equipment, said biomedical electrode comprising:
said first electrical node including a disc of conductive material having a diameter $d_1$;
said second electrical node including a first ring of conductive material, said first ring being concentric with the disc and having a radius a that is larger than $d_1/2$; and
said third electrical node including a second ring of conductive material, said second ring also being concentric with the disc and having a radius β that is larger than α;
said fourth electrical node including a third ring of conductive material, said third ring also being concentric with the disc and having a radius of thirty millimeters that is larger than β, such that $(3\alpha\beta)^2$ is less than about 0.225 cm$^4$.

14. The biomedical electrode as claimed in claim 13, wherein at least two of the first, second, third and fourth electrical nodes are coupled together.

15. The biomedical electrode as claimed in claim 13, wherein said first ring of conductive material of said second electrical node has a ring thickness $t_2$ such that ($4 \leq d_1/t_2 \leq 5$).

16. The biomedical electrode as claimed in claim 15, wherein said second ring of conductive material of said third electrical node has a ring thickness $t_3$ such that ($4 \leq d_1/t_3 \leq 5$).

17. A fabric of a garment including the biomedical electrode as claimed in claim 13.

18. A fabric of a garment including an array of biomedical electrodes, each of which is a biomedical electrode as claimed in claim 13.

* * * * *